(12) United States Patent
Louie et al.

(10) Patent No.: US 8,092,828 B2
(45) Date of Patent: Jan. 10, 2012

(54) FIXED DRUG RATIOS FOR TREATMENT OF HEMATOPOIETIC CANCERS AND PROLIFERATIVE DISORDERS

(75) Inventors: Arthur Louie, Princeton, NJ (US); Christine Swenson, Princeton Jct, NJ (US); Lawrence Mayer, North Vancouver (CA); Andrew Janoff, Yardley, PA (US)

(73) Assignee: Celator Pharmaceuticals, Inc., Princeton, NJ (US)

( * ) Notice: Subject to any disclaimer, the term of this patent is extended or adjusted under 35 U.S.C. 154(b) by 411 days.

(21) Appl. No.: 12/032,583

(22) Filed: Feb. 15, 2008

(65) Prior Publication Data

US 2008/0199515 A1 Aug. 21, 2008

Related U.S. Application Data

(60) Provisional application No. 60/901,772, filed on Feb. 16, 2007, provisional application No. 60/965,196, filed on Aug. 17, 2007.

(51) Int. Cl.
*A61K 9/127* (2006.01)
*A61K 31/00* (2006.01)

(52) U.S. Cl. ............................. 424/450; 514/1

(58) Field of Classification Search ............ 424/450; 514/1
See application file for complete search history.

(56) References Cited

U.S. PATENT DOCUMENTS

| 2004/0152632 | A1* | 8/2004 | Feingold .......................... 514/12 |
| 2006/0057111 | A1  | 3/2006 | Hedlund et al. |
| 2006/0165649 | A1  | 7/2006 | Zeldis |
| 2006/0165771 | A1  | 7/2006 | Tardi et al. |
| 2007/0286897 | A1* | 12/2007 | Mayer et al. .................. 424/450 |

FOREIGN PATENT DOCUMENTS

| WO | WO-2004/093795 | 11/2004 |
| WO | WO-2005/102359 | 11/2005 |
| WO | WO-2007/076117 | 7/2007 |

OTHER PUBLICATIONS

Kawasaki et al, Blood 98(13):3589-3594, 2001.*
Freund et al, Cancer Chemother. Pharmacol. 28:487-490, 1991.*
Mayer et al., Mol. Cancer Ther. (2006) 5:1854-1863.
Tallman et al., Blood (2005) 106:1154-1163.
International Search Report and Written Opinion for PCT/US08/54168, mailed Jul. 7, 2008, 6 pages.
Foudi et al., "Reduced retention of radioprotective hematopoietic cells within the bone marrow microenvironment in CXCR4−/− chimeric mice" in Blood (2006) 107(6):2243-2251.
Johnstone et al., "Synergistic antitumor activity observed for a fixed ratio liposome formulation of Cytarabine (Cyt):Daunorubicin (Daun) against preclinical leukemia models" in Proceedings of the Annual Meeting of the American Association for Cancer Research (2005) 46:Abstract 1405.
Supplementary European Search Report for EP Application No. 08730048.9, mailed on Mar. 23, 2010, 7 pages.

* cited by examiner

*Primary Examiner* — Kevin K. Hill
(74) *Attorney, Agent, or Firm* — Morrison & Foerster LLP (57) ABSTRACT

Provided herein are methods for treating cancer by administering a pharmaceutical composition comprising a fixed, non-antagonistic molar ratio of cytarabine and an anthracycline. Such methods are particularly useful in the treatment of patients with advanced hematologic cancers or proliferative disorders.

11 Claims, 1 Drawing Sheet

Mean plasma concentration after the day 5 infusion among patients receiving 24 units/m^2 CPX-351 (n=3)

Figure 1A

Plasma molar ratio of cytarabine to daunorubicin after the day 5 infusion among patients receiving 24 units/m^2

Figure 1B dose_cytarabine=57, day=5

Figure 1C

FIXED DRUG RATIOS FOR TREATMENT OF HEMATOPOIETIC CANCERS AND PROLIFERATIVE DISORDERS

RELATED APPLICATIONS

The application claims priority from U.S. Application Ser. No. 60/901,772 filed 16 Feb. 2007, and U.S. Application Ser. No. 60/965,196 filed 17 Aug. 2007, each of which is incorporated herein by reference in its entirety.

TECHNICAL FIELD

The invention relates to methods for improved delivery and therapeutic effectiveness of a combination of therapeutic agents. More particularly, the inventions relates to delivery of a fixed ratio combination of cytarabine and an anthracycline, e.g., daunorubicin.

BACKGROUND ART

In vitro studies have shown that antitumor activity can be enhanced when cytotoxic drugs are used in combination. This has led, over the years, to the use of drug combinations in the clinic such that cytotoxic drug combinations are now standard in many forms of cancer chemotherapy. New anticancer drugs are typically first introduced in patients as single agents. After a maximum tolerated dose is determined for one agent, a second agent is added and the dose of one or both agents is adjusted on the basis of toxicity. Usually the more active or efficacious agent is used at full dose and the other agent is dose reduced and titrated upward in dose until dose limiting toxicity defines the maximum tolerated dose for the combination. As a result the development of most combination regimens is determined empirically on the basis of tolerability. However, in vitro, where the molar ratio of drugs used in combination can be controlled, it has been demonstrated that drug combinations providing synergy at one ratio may be simply additive or even antagonistic at other ratios (Mayer, L. D., et al., *Mol. Cancer. Ther.* (2006) 5:1854-1863). When individual free drugs are administered in chemotherapy "cocktails", each agent is handled differently by the body, resulting in varying distribution and elimination of each drug, which can result in drug ratios that are suboptimal or ineffective for some or most of the time. The observation that in vitro synergistic activity of antineoplastic drugs depends on specific drug ratios suggests that the in vivo and clinical activity of a combination may be enhanced by maintaining the synergistic ratio. In this way, the development of particular combination chemotherapeutic regimens can be based on the most efficacious ratio rather than empirically based on toxicity.

Combination chemotherapies comprising cytidine analogues and anthracycline agents have been well studied for treatment against various cancers or hematologic proliferative disorders. Drug cocktails of the cytidine analogue, cytarabine, and an anthracycline such as daunorubicin demonstrate some efficacy in patients with hematologic malignancies. See, e.g., Tallum, et al., *Blood* (2005) 106: 2243. Since 1973, cytarabine combined with an anthracycline has been the standard first-line therapy for acute myelogenous leukemia (AML), against which other regimens are compared. At present, the standard of care for AML is a combination of cytarabine and daunorubicin administered in the classic "7 and 3" regimen with cytarabine administered for 7 consecutive days and daunorubicin for the first 3 of those 7 consecutive days.

Cytarabine (cytosine arabinoside, Ara-C or 1-β-D-arabinofuranosylcytosine) is a cell cycle phase-specific antineoplastic agent, affecting cells predominantly during the S-phase of cell division. Intracellularly, cytarabine is converted into cytarabine-5'-triphosphate (ara-CTP), which is the active metabolite. The mechanism of action is not completely understood, but it appears that ara-CTP acts primarily through inhibition of DNA polymerase. Incorporation into DNA and RNA may also contribute to cytarabine cytotoxicity. Cytarabine is cytotoxic to a wide variety of proliferating mammalian cells in culture.

Daunorubicin hydrochloride is the hydrochloride salt of an anthracycline cytotoxic antibiotic produced by a strain of *Streptomyces coeruleorubidus*. Daunorubicin has antimitotic and cytotoxic activity through a number of proposed mechanisms of action. Daunorubicin forms complexes with DNA by intercalation between base pairs. It inhibits topoisomerase II activity by stabilizing the DNA-topoisomerase II complex, preventing the religation portion of the ligation-religation reaction that topoisomerase II catalyzes. Single strand and double strand DNA breaks result. Daunorubicin may also inhibit polymerase activity, affect regulation of gene expression, and produce free radical damage to DNA. Daunorubicin possesses an antitumor effect against a wide spectrum of animal tumors, either grafted or spontaneous.

While combinations of these two drugs administered as drug cocktails have provided some benefit, there are various drawbacks that limit their therapeutic use. For instance, administration of free drug cocktails typically results in rapid clearance of one or all of the drugs before reaching the disease site. If the individual drugs in the cocktail are only optimally effective within a narrow ratio to one another, a rapid clearance of one drug but not the other can reduce overall efficacy of the combination while increasing toxicity. This can sometimes lead to increased toxicity as individual drug dosages are increased to achieve a greater therapeutic effect. Attempts to improve activity and reduce toxicity also can include longer infusion times. For example, the current administration of cytarabine which is either given in high doses (1 gram/m$^2$/day) by slow bolus over 1 hour/day or in lower, more typical, doses (100-200 mg/m$^2$/day) by continuous infusion for the 7 consecutive days. Such long infusional administration results in increased complexity, hospitalization time, and expense as well as increased risk of infusion complications.

Addition of other agents such as 6-thioguanine or etoposide and changes in the dose or schedule of administration have been studied to improve outcomes, but while incremental gains have been made, the 30-year old use of an anthracycline and cytarabine remains the basis for standard induction treatment in AML. Therefore, in order to substantially improve overall survival in the disease along with lowered toxicity, there is a need for more effective and better-tolerated induction and/or consolidation therapies.

Drug delivery regimens for these agents, such as those identified here, that permit the sustained delivery of non-antagonistic drug ratios are highly desirable as they will permit reduced administration times without increasing toxicity or decreasing efficacy of the treatment. Such improvements in regimens may also permit more effective doses to be administered to the patient than would be possible with other regimens that otherwise are limited by toxicity.

DISCLOSURE OF THE INVENTION

In one aspect, provided herein is a method to treat cancer or hematologic proliferative disorder in a subject, said method comprising administering to said subject a pharmaceutical composition comprising a fixed, non-antagonistic molar ratio of cytarabine and an anthracycline such as daunorubicin, wherein the ratio of cytarabine:anthracycline is maintained at a non-antagonistic ratio in the plasma for at least about 4 hours. In another embodiment, the fixed, non-antagonistic molar ratio is maintained for at least about 8 hours, at least about 16 hours, or at least about 24 hours. The anthracycline can be daunorubicin or mitoxantrone. In a specific embodiment, the anthracycline is daunorubicin. Typically, the cytarabine and anthracycline are stably associated with one or more delivery vehicles. Encapsulation in delivery vehicles allows two or more agents to be delivered to the disease site in a coordinated fashion, thereby assuring that the agents will be present at the disease site at a non-antagonistic ratio. This result will be achieved whether the agents are co-encapsulated in delivery vehicles, or are separately encapsulated in delivery vehicles administered such that non-antagonistic ratios are maintained at the disease site. The pharmacokinetics (PK) of the composition are controlled by the delivery vehicles themselves such that coordinated delivery is achieved (provided that the PK of the delivery systems are comparable). In one embodiment, the delivery vehicle is a liposome.

In another aspect, provided herein is a method to treat cancer or hematologic proliferative disorder in a subject, said method comprising administering to said patient a pharmaceutical composition comprising a fixed, non-antagonistic molar ratio of cytarabine and anthracycline, wherein said composition is administered intravenously. In some embodiments, the pharmaceutical composition is administered in at least about 30 minutes and usually less than about 8 or 12 hours. In a specific embodiment, the pharmaceutical composition is administered in about 90 minutes. In another embodiment, the pharmaceutical composition is administered on an out-patient basis. The anthracycline can be daunorubicin, idarubicin or mitoxantrone. In a specific embodiment, the anthracycline is daunorubicin.

In one aspect, provided herein is a method to treat cancer or hematologic proliferative disorder in a subject in need thereof, said method comprising administering to said patient a pharmaceutical composition comprising a fixed, non-antagonistic molar ratio of cytarabine and an anthracycline, wherein cytarabine is administered in low doses at less than 250 mg/m$^2$/day in less than 3 hours. In a specific embodiment, the cytarabine is administered at about 100-180 mg/m$^2$/day in less than 3 hours. In another embodiment, the low-dose cytarabine is administered in about 90 minutes.

In one aspect, provided herein is a method to reduce the toxicity of cytarabine/anthracycline combination chemotherapy treatments in a subject by administering to said patient a pharmaceutical composition comprising delivery vehicles having stably associated therewith a fixed, non-antagonistic molar ratio of cytarabine and anthracycline, wherein the toxicity resulting from administration of said composition is less than the toxicity that results from administration of the same amount of cytarabine and anthracycline when not present in delivery vehicles. In some embodiments, reduction in toxicity is measured as a reduction in non-hematopoietic toxicities such as, for example, mucositis or alopecia. A reduction in such toxicities can in turn lead to a reduction in hospitalization, supportive care, morbidity and/or a reduction in induction mortality particularly in patients over 60 years of age and more specifically in patients over the age of 75.

In the methods provided herein, the fixed, non-antagonistic molar ratio of cytarabine and anthracycline can be between about 25:1 and about 1:1. In a specific embodiment, the fixed, non-antagonistic ratio of cytarabine:anthracycline is about 5:1. Typically, the combination of cytarabine and anthracycline at a fixed, non-antagonistic ratio is encapsulated in a liposome.

In some embodiments, the cancer is an advanced hematologic cancer. The advanced hematologic cancer can be acute lymphocytic leukemia (ALL), acute myeloid leukemia (AML) or acute promyelocytic leukemia (APL). In one embodiment, the hematologic proliferative disorder is myelodysplastic syndrome (MDS). Sometimes, the cancer is a relapsed cancer. The subject can previously have undergone at least one anti-tumor regimen. In one embodiment, the patient has failed or become refractory to one or more anti-tumor regimens. Sometimes, the prior anti-tumor regimen is a multi-agent regimen. In one embodiment, the prior anti-tumor regimen consists of cytarabine with or without an anthracycline.

In further embodiments, provided herein is a post-remission therapy for cancer or hematologic proliferative disorder in a subject in need thereof, said method comprising administering to said patient a pharmaceutical composition comprising a fixed, non-antagonistic molar ratio of cytarabine and an anthracycline, wherein said post-remission therapy is administered less than 18 months after a same or different treatment. In a specific embodiment, the post-remission therapy is administered less than 6 months after a same or different treatment. In a further embodiment, the post-remission therapy is administered to patients with relapsed AML, ALL or APL. In one embodiment, the post-remission therapy consists of cytarabine with or without an anthracycline.

In additional embodiments, provided herein is a first line therapy for cancer or hematologic proliferative disorder in a subject in need thereof, said method comprising administering to said patient a pharmaceutical composition comprising a fixed, non-antagonistic molar ratio of cytarabine and an anthracycline, wherein cytarabine is administered in low doses at less than 250 mg/m$^2$/day in less than 3 hours. In a specific embodiment, the first line therapy is provided for high-risk patients, preferably, elderly high-risk patients. In a further embodiment, cytarabine is administered at about 100 mg/m$^2$/day or less to high-risk patients.

Also contemplated is the use of a pharmaceutical composition comprising a fixed, non-antagonistic molar ratio of cytarabine and an anthracycline, wherein the cytarabine:anthracycline ratio is maintained at a non-antagonistic ratio in the plasma for at least about 4 hours, to treat a subject with cancer or hematologic proliferative disorder as disclosed herein. In another aspect, provided herein is the use of the disclosed pharmaceutical compositions comprising a fixed, non-antagonistic molar ratio of cytarabine and an anthracycline for the preparation of a medicament to treat cancer or hematologic proliferative disorder, wherein said fixed, non-antagonistic molar ratio is maintained in the plasma for at least about 4 hours, to treat a subject with cancer as disclosed herein.

BRIEF DESCRIPTION OF THE DRAWINGS

FIG. 1 shows the plasma drug concentrations and sustained fixed molar ratio of cytarabine:daunorubicin in the plasma following administration of the liposomal-encapsulated cytarabine and daunorubicin. A. Mean concentration of cytarabine and daunorubicin in the plasma of patients after day-5 infusion (on a day 1, 3 and 5 CPX-351 administration cycle) of 24 units/m$^2$ of CPX-351 up to 7 days (concentrations determined by LC-MS/MS; Each line represents a single patient; N=3). B. Molar ratio of cytarabine and daunorubicin in the plasma of patients after day-5 infusion of 24 units/m² of CPX-351 up to 24 hours (concentrations determined by LC-MS/MS; Each line represents a single patient; N=3). C. Molar ratio of cytarabine and daunorubicin in the plasma of patients after day-5 infusion of 57 units/m² of CPX-351 up to 48 hours (concentrations determined by LC/MS/MS; Each line represents a single patient; N=3).

MODES OF CARRYING OUT THE INVENTION

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

For cytarabine and anthracycline, the non-antagonistic molar ratio in vitro was between 25:1 and about 1:1, where a molar ratio of 5:1 was found to be optimal. Any suitable anthracycline can be employed. The anthracycline can be daunorubicin, idarubicin or mitoxantrone. In a specific embodiment, the anthracycline is daunorubicin. The development of CPX-351 (cytarabine:daunorubicin) liposome injection was based on 1) defining a non-antagonistic ratio of the two active moieties, cytarabine and daunorubicin, using cell-based screening assays and 2) designing a liposomal drug carrier to maintain this ratio after intravenous administration. This ratio was not based on the empirically-derived regimens currently used for cytarabine and anthracyclines.

Provided herein are methods to deliver fixed, non-antagonistic molar ratios of cytarabine and an anthracycline to enhance anti-tumor activity while providing the advantages of rapid administration. In brief, non-antagonistic ratios of these chemotherapeutic agents were determined in vitro using cell-based screening techniques. If these same ratios are administered separately as free drug cocktails (e.g., conventional aqueous-based pharmaceutical formulations without liposome delivery), the ratio is not maintained because the drugs are distributed and eliminated independently of one another, resulting in a continuously changing ratio. Using encapsulated drugs in liposomes, the methods provided herein permit maintenance of the non-antagonistic ratio after administration for extended periods of time. The liposomal formulation delivers each drug in correct proportion by controlling the individual pharmacokinetics of each drug and thereby sustaining the non-antagonistic ratio.

Typically, sustained delivery requires a greater amount of a drug being administered in an effort to maintain a therapeutically effective level of the drug in the plasma and ultimately in the tumor or disease site. Such large doses are administered over a long period of time, often one or more days, requiring long hospital stays and/or reliance on prolonged infusion protocols that increase the risk of complications such as infection or pump malfunction. Another disadvantage is that toxicity resulting from the higher doses may prevent an optimal plasma level from being achievable.

CPX-351 is a liposomal formulation with a fixed 5:1 molar ratio of cytarabine and daunorubicin and has shown enhanced efficacy in cell culture and in in vivo models. (Mayer, L. D. et al., *Mol. Cancer. Ther.* (2006) 5:1854-1863). Any suitable source of cytarabine (also known as 4-amino-1-[(2R,3S,4R,5R)-3,4-dihydroxy-5-(hydroxymethyl)oxolan-2-yl] pyrimidin-2-one or 1β-arabinofuranosylcytosine) and daunorubicin (also known as (8S,10S)-8-acetyl-10-[(2S,4S,5S,6S)-4-amino-5-hydroxy-6-methyl-oxan-2-yl]oxy-6,8,11-trihydroxy-1-methoxy-9,10-dihydro-7H-tetracene-5,12-dione or daunomycin cerubidine) can be employed.

Any suitable delivery vehicle can be employed that permits the sustained delivery of cytarabine:daunorubicin combination at a fixed, non-antagonistic molar ratio provided herein. In one embodiment, a single delivery vehicle is employed. In other embodiments, the active agents are delivered in separate delivery vehicles that maintain the desired non-antagonistic ratios of agents. In some embodiments, a liposomal formulation may be employed. The liposomes are designed for sustained delivery of the encapsulated drugs at a non-antagonistic ratio to a tumor or disease site. In one embodiment, cytarabine and daunorubicin are stably associated with one or more liposomes. Typically, the liposomes have an average diameter of less than 300 nm, sometimes less than 200 nm. In one example, the nominal size of these liposomes is approximately 100 nm and sterilization is achieved by filtration through a 0.2 μm filter. In a specific embodiment, the liposome membrane is composed of distearoylphosphatidylcholine (DSPC), distearoylphosphatidylglycerol (DSPG) and cholesterol (CHOL) in a 7:2:1:molar ratio. In one instance, the liposomes are prepared by a water-in-oil derived liposome method and extruded liposomes are suspended in phosphate-buffered sucrose at pH 7.4. In specific embodiments, the cytarabine to lipid ratio is from about 1:1.5 to 1:2.6 and the daunorubicin to lipid ratio is from about 1:7.7 to 1:12.5. Preferably the cytarabine to lipid ratio is about 1:2 and the daunorubicin to lipid ratio is 1:10. Exemplary delivery vehicles include, but are not limited to those described in Torchilin, et al. (eds.), *Liposomes: A Practical Approach* (Oxford University Press 2nd ed. 2003); Gregoriadis, *Liposome Technology* (Taylor & Francis 3rd Ed. 2006). Any suitable means of encapsulating the drug combination in the liposomes can be employed. In a specific embodiment, cytarabine and daunorubicin are encapsulated in the liposome whereby the cytarabine is passively encapsulated into pre-formed liposomes and the daunorubicin is actively accumulated inside the liposomes at high trapping efficiencies using a copper gluconate/triethanolamine-based loading procedure. See, e.g., copending PCT Application No. WO 07/076,117.

The methods provided herein are useful in any subject, particularly humans with cancer or advanced hematologic tumors or disorders. Cancer encompasses any malignant cell with abnormal, uncontrolled growth. Such cells possess a number of characteristic properties such as uncontrolled proliferation, immortality, metastatic potential, rapid growth and proliferation rate, and certain typical morphological features. Often, cancer cells will be in the form of a tumor, but such cells may also exist alone within a mammal, or may be a non-tumorigenic cancer cell, such as a leukemia cell. A cell is identified as cancer by any of a number of ways, including, but not limited to, detecting the presence of a tumor or tumors (e.g., by clinical or radiological means), examining cells within a tumor or from another biological sample (e.g., from a tissue biopsy), measuring blood markers indicative of cancer (e.g., CA125, PAP, PSA, CEA, and the like), and/or detecting a genotype indicative of a cancer (e.g., TP53, ATM, and the like). The term "hematopoietic tumors" refers to tumors or cancers of the blood. As used herein, the term "advanced hematopoietic tumors" refers to a malignant tumor that is in relapse or is refractory to one or more previous anti-tumor regimens. Hematopoietic tumors can be a leukemia or a lymphoma. Such tumors include acute myelogenous leukemia (AML), acute lymphocytic leukemia (ALL), acute promyelocytic leukemia (APL), precursor and mature B cell neoplasms, chronic lymphocytic leukemia (CLL), plasma cell neoplasms, chronic myelocytic leukemia (CML), multiple myeloma, Hodgkin's lymphoma, non-Hodgkin's lymphoma, myelodysplastic syndromes (MDS), myelodysplastic and myeloproliferative diseases, chronic myelomonocytic leukemia (CMML), polycythemia vera, precursor and mature T cell neoplasms, T cell leukemias and lymphomas, mycosis fungoides, and Sezary syndrome. See, e.g., a summary of hematopoietic and lymphoid malignancies at Greer, et al. (eds.), *Wintrobe's Clinical Hematology* (Lippincott Williams & Wilkins 11th Ed. (2003)) at Table 71.3 (World Health Organization Classification of Hematopoietic and Lymphoid Neoplasms). The tumors treated using the compositions provided herein include those in adult and pediatric patients. The compositions can be employed in induction and maintenance therapy. The disclosed compositions are also useful in related hematologic disorders such as myelofibrosis and amyloidosis due to light chain disease. More particularly, AML can include those with recurrent genetic abnormalities (regardless of % blasts) such as AML with t(8; 21)(q22;q22), (AML1/ETO), AML with abnormal bone marrow eosinophils and inv(16)(p13q22) or t(16:16)(p13;q22), (CBFβ/MYH11), acute promyelocytic leukemia with or t(15; 17) (q22;q12), (PML/RARα) and variants and AML with 11q23 (MLL) abnormalities; AML with multilineage dysplasia (minimum 20% blasts) such as following MDS or MDS/MPD, without antecedent MDS or MDS/MPD, but with dysplasia in at least 50% of cells in 2 or more myeloid lineages; AML and MDS that is therapy related (minimum 20% blasts) such as alkylating agent/radiation-related type and topoisomerase II inhibitor-related type (some may be lymphoid) as well as AML not otherwise classified.

The methods disclosed herein provide for a sustained delivery of a fixed, non-antagonistic molar ratio of cytarabine and daunorubicin. For example, the non-antagonistic molar ratio for cytarabine:daunorubicin in the plasma is maintained for up to at least about 4 hours, at least about 8 hours, at least about 12 hours, at least about 16 hours, and often at least about 24 hours following a single administration of the drug combination. In addition, the sustained concentration of the liposomal encapsulated-drug combination in the plasma is greater than the drug concentration of the free cocktail drug combination in the plasma.

By "maintained" or "maintain", it is meant that the drug:drug ratio changes by less than 5 fold, preferably less than 4 fold, less than 3 fold, and most preferably, by less than 2 fold.

The disclosed methods are also therapeutically effective in treating relapsed cancer. A "relapsed cancer" refers to a cancer that has recurred following prior complete or partial remission in response to a prior treatment. Recurrence can be defined in any way, including a reappearance or re-growth of tumor cells as detected by clinical, radiological, or biochemical assays, or by an increased level of a cancer marker. Prior treatments can include, but are not limited to chemotherapy, biological or hormonal therapies, radiation therapy, and bone marrow transplantation.

In some embodiments, the patients treated with the methods provided herein are those that have previously been treated with, progressed following, or are resistant to other therapies. For example, patients can be treated with the methods provided herein after receiving or becoming resistant to any chemotherapy or biological therapy. For example, in some patients, they may have previously received one or more of the following agents: cyclophosphamide, prednisone, methylprednisolone, imatinib, ifosfamide, methotrexate, leucovorin, vincristine, cytarabine, etoposide, dexamethasone, doxorubicin, daunorubicin, asparaginase, 6-mercaptopurine, 6-thioguanine, carboplatin, fludarabine, gemtuzumab, arsenic trioxide, tretinoin, idarubicin, mitoxantrone, alemtuzumab, chlorambucil, cladribine, rituximab, pentostatin, hydroxyurea, interferon alfa 2B, nelarabine and azacytidine.

In specific embodiments, the patients treated with the methods provided herein are those that have been treated with, progressed following, or are resistant to other therapies which were administered less than 18 months prior, or more specifically, less than 12 months prior, or even more specifically, less than 6 months prior. This is true even if the patient has relapsed within this time.

In some cases the patients have experienced a relapse within 18, 12 or 6 months after said prior treatment. In some cases said prior treatment includes cytarabine and an anthracycline.

The methods disclosed herein can also be employed as a first line therapy for cancer or hematologic cancer that have not previously been treated. In specific embodiments, the first line therapy is administered to high-risk patients, more specifically, high-risk elderly patients. In some embodiments, high-risk patients receive doses of cytarabine that are about 100 mg/m$^2$/day or less.

Responses to the disclosed therapeutic methods include any clinically evident, positive change in hematologic cancer or disorder disease state. Such responses can include complete or partial remission, increases in overall survival and increases in progression-free survival. Disease responses are assessed by any suitable means. For example, for AML, ALL, and myelodysplastic syndromes complete remission requires normalization of peripheral blood neutrophils to $\geq 1000$/dL, platelets to more than 100,000/dL and normocellular bone marrow with less than 5% blasts with no Auer rods. If Auer rods are present with less than 5% blasts then the response is considered partial. Responses are considered partial if there is normalization in peripheral blood neutrophil and platelet counts but 6-25% blasts persist in bone marrow. The duration of overall response can be measured from the time when response criteria are first met for complete remission (CR) or partial remission (PR) (whichever is first recorded) until the first date that recurrent or progressive disease is documented. Response duration can be measured from the time measurement criteria for CR or PR are first met until the first date that recurrent or progressive disease is objectively documented.

The pharmaceutical compositions provided herein are administered to any suitable subjects, preferably human subjects with cancer. Preferably, the pharmaceutical compositions of the present invention are administered intravenously. Dosage for the delivery vehicle formulations will depend on the administrating physician's opinion based on age, weight, and condition of the patient.

While individual judgment may vary on the part of the physician, it has been surprisingly found that sufficient dosage of the fixed ratio combination of the invention can be obtained using substantially shorter times in substantially lower dosages than those currently employed in the standard of care protocols that involve cytarabine and daunorubicin. As noted above, the "7 and 3" regimen has cytarabine administered 24 hours per day for 7 consecutive days and daunorubicin, by IV, for the first 3 of those 7 consecutive days. This means that the patient must be connected to a continuous infusion pump for administration of the cytarabine rather than an IV drip. The use of these pumps increases the risk of inadequate delivery of the drug(s) since it has been noted that the pumps, which are pre-loaded with the entire 7 days worth of cytarabine, can malfunction and release all 7 days worth of drug at one time or, alternatively, not release any drug. Patients using a pump must also check in daily at the hospital so that the pump can be inspected, this increases hospital costs as well as patient inconvenience. It has been found that the compositions of the invention with fixed ratio of cytarabine:daunorubicin or other anthracycline at a fixed non-antagonistic ratio may be administered in much shorter times, typically 12 hours or less, 8 hours or less, and more typically 3 hours or less. The achievement of infusion times of this magnitude, especially 8 hours or less permits administration on an outpatient basis. It also permits administration by IV drip rather than with an infusion pump. These parameters further reduce the risk of the patient having an infusion reaction.

Thus, the method of the invention, which requires infusion times by IV drip of less than 12 hours or less, preferably 8 hours or less, more preferably 3 hours or less, is advantageous from the standpoint of patient convenience and safety.

Pharmaceutical compositions comprising delivery vehicles of the invention are prepared according to standard techniques and may comprise water, buffered water, 0.9% saline, 0.3% glycine, 5% dextrose and the like, including glycoproteins for enhanced stability, such as albumin, lipoprotein, globulin, and the like. These compositions may be sterilized by conventional, well-known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and the like. Additionally, the delivery vehicle suspension may include lipid-protective agents which protect lipids against free-radical and lipid-peroxidative damages on storage. Lipophilic free-radical quenchers, such as alpha-tocopherol, ascorbyl palmitate and water-soluble iron-specific chelators, such as ferrioxamine, are suitable.

The results of the method of the invention are typically more efficacious than those afforded by the "standard of care" protocol. In the "standard of care protocol" cytarabine is administered at a dosage level of 100-200 mg/m$^2$/day by continuous infusion over 7 days with daunorubicin being administered IV at a dose of 45-60 mg/m$^2$ for the first 3 days of this regimen.

The concentration of delivery vehicles in the pharmaceutical formulations can vary widely, such as from less than about 0.05%, usually at or at least about 2-5% to as much as 10 to 30% by weight and will be selected primarily by fluid volumes, viscosities, and the like, in accordance with the particular mode of administration selected. For example, the concentration may be increased to lower the fluid load associated with treatment. Alternatively, delivery vehicles composed of irritating lipids may be diluted to low concentrations to lessen inflammation at the site of administration. For diagnosis, the amount of delivery vehicles administered will depend upon the particular label used, the disease state being diagnosed and the judgment of the clinician.

The safety of the procedure can be adjusted by assessing side effects, such as alopecia, cellulitis, injection site or extravasation reactions, or mucositis. Mucositis can be measured by oral or anal inflammation or ulceration; by esophageal ulceration or esophagitis; nausea, vomiting or diarrhea; and by anorexia. Side effects are reduced by avoiding an indwelling line for extended periods of time.

The following examples are offered to illustrate but not to limit the invention.

EXAMPLE 1

In Vivo Studies with CPX-351

The toxicology of CPX-351 (Cytarabine:Daunorubicin) Liposome Injection has been studied in rats and dogs given single doses and repeated (every other day for 3 doses, repeated after 2 weeks) doses.

Single dose studies. In the single dose studies (Table 1), CPX-351 was administered by intravenous infusion over one hour and animals were observed for 14 days. The "vehicle control" consisted of liposomes containing copper gluconate but no drugs. There was no drug-related mortality in rats receiving a single dose of CPX-351. Dose-related changes in various hematology parameters and splenic and hepatic extramedullary hematopoiesis were noted on day 15 in both male and female mid and high dose groups compared with control rats. The no-observed-adverse-effect levels (NOAEL) for single dose CPX-351 in rats was 10 mg/kg cytarabine:4.4 mg/kg daunorubicin. In dogs administered a single dose of CPX-351, poor condition led to the pre-terminal sacrifice of both high dose (6 mg/kg cytarabine:2.64 mg/kg daunorubicin) animals and the mid-dose (3 mg/kg cytarabine: 1.32 mg/kg daunorubicin) female between days 8 and 10 after dosing. Prior to sacrifice, these dogs showed severely reduced food intake and weight loss as well as severely decreased white blood cell and platelet counts. Histopathological findings in dogs terminated early included lymphoid hypocellularity, atrophy of the spleen and thymus and necrosis/hemorrhage in the GI tract. There were no drug-related clinical signs in animals receiving the low dose (1.5 mg/kg cytarabine:0.66 mg/kg daunorubicin) or the vehicle control. There were no drug-related changes in hematology, clinical chemistry, coagulation, urinalysis or macroscopic evaluation in animals surviving to scheduled termination. In the mid-dose male, there was microscopic evidence of lymphoid hypocellularity and atrophy of the spleen. Whole blood copper concentrations on day 2 (~24 hours post-treatment) were elevated in a dose-related manner in all animals receiving CPX-351, but returned to normal levels by days 8-15.

TABLE 1

Summary of Single Dose Toxicological studies with CPX-351

| Study # | Species/strain (route) | Regimen | Duration of study | Evaluations | Group | Cytarabine Dose (mg/kg) | Daunorubicin Dose (mg/kg) Free base | Deaths/Total M | F | comments |
|---|---|---|---|---|---|---|---|---|---|---|
| 3004-3322 | dog/beagle (iv) | Weekly 60 minute infusion | 5 weeks | Mortality, clinical signs, body weight, food consumption | Day 1 Day 8 Day 15 Day 22 | 1 2 3 4 | 0.44 0.88 1.32 1.76 | | 0/1 | Pilot Study conducted in a single dog. ↓ food consumption, ↓ activity after 3 mg/kg dose. No clinical signs after 4 mg/kg dose. |

TABLE 1-continued

Summary of Single Dose Toxicological studies with CPX-351

| Study # | Species/ strain (route) | Regimen | Duration of study | Evaluations | Group | Cytarabine Dose (mg/kg) | Daunorubicin Dose (mg/kg) Free base | Deaths/Total M | F | comments |
|---|---|---|---|---|---|---|---|---|---|---|
| 1004-3331 | rat/SD (iv) | single 60 minute infusion | 14 days | mortality, clinical signs, body weight, hematology, serum chemistry (copper), urinalysis, gross pathology, selected micro pathology | 1 saline<br>2 CPX-351<br>3 CPX-351<br>4 CPX-351<br>5 CPX-351 | 0<br>5<br>10<br>15<br>20 | 0<br>2.2<br>4.4<br>6.6<br>8.8 | 0/5<br>0/5<br>0/5<br>0/5<br>0/5 | 0/5<br>0/5<br>0/5<br>0/5<br>0/5 | There were no test article-related findings in clinical signs, body weights, coagulation, clinical chemistry or urinalysis. Slight to moderate ↓ in WBC, RBC and lymphocytes in groups 4 and 5. Drug-related ↑ in spleen and liver extramedullary hematopoiesis. |
| 1004-3342 | dog/ beagle (iv) | single 60 minute infusion | 14 days | mortality, clinical obs, body weight, food consumption, hematology, serum chemistry (copper), urinalysis, gross pathology, selected micropathology | 1 saline<br>2 vehicle<br>3 CPX-351<br>4 CPX-351<br>5 CPX-351 | 0<br>0<br>1.5<br>3.0<br>6.0 | 0<br>0<br>0.66<br>1.32<br>2.64 | 0/1<br>0/1<br>0/1<br>0/1<br>1/1* | 0/1<br>0/1<br>0/1<br>1/1<br>1/1 | Clinical signs were ↓ food consumption, retching, vomiting, diarrhea, hypoactivity, dehydration, pale gums, ↓ body weight in groups 4-5. Animals terminated early showed marked lymphoid hypocellularity, atrophy of spleen, glandular necrosis, hemorrhage in GI tract, ↓↓ WBC, ↓↓ platelets. No treatment-related gross or microscopic findings in groups 2 and 3. |

*Terminated due to poor condition on Day 8
**Terminated due to poor condition on Day 10

Repeat-dose Studies. In the repeated dose studies (planned dosing on days 1, 3, 5 and 22, 24 and 26; [Table 2]), there was drug-related mortality in both rats and dogs. In rats, the underlying pathology leading to early termination or death in groups 3 (10 mg/kg cytarabine:4.4 mg/kg daunorubicin) and 4 (15 mg/kg cytarabine:6.6 mg/kg daunorubicin) was marked or severe hematopoietic hypocellularity of the bone marrow and lymphoid hypocellularity/atrophy of the spleen and thymus. There was also necrosis of the glandular and crystal epithelium of the large and small intestinal mucosa in animals that died or were sacrificed early. When compared to mean control values obtained on day 34 (7 days after the last dose), a moderate drug-related reduction in WBC counts was noted in group 2 (5 mg/kg cytarabine:2.2 mg/kg daunorubicin) rats. The animals in the high dose group (group 4) that were assigned to the recovery group were all found dead or sacrificed early (between days 10 and 16) therefore, reversibility of the cytotoxic effects of CPX-351 could not be demonstrated in this study.

Following the first dosing cycle, all dogs in the high dose CPX-351 group (group 5; 3 mg/kg cytarabine: 1.32 mg/kg daunorubicin) were either found dead (2 males) or were sacrificed due to poor condition between days 7 and 10. Two dogs in the mid-dose group (group 4, one male and one female) were sacrificed in poor condition on day 12. The probable cause of death in the dogs found dead and the main underlying affliction of those that underwent unscheduled sacrifice was considered to be severe bone marrow hypocellularity and/or moderate to severe enteric (duodenum, jejunum, ileum, cecum, colon and rectum) crystal/glandular necrosis and lymphoid atrophy of gut-associated lymphoid tissue.

Decreases in peripheral blood white blood cells were evident in animals in group 3 (1 mg/kg cytarabine:0.44 mg/kg daunorubicin) and group 6 (free cytarabine 2 mg/kg and free daunorubicin 0.88 mg/kg) at day 33 (6 days after their last dose of CPX-351 or the free drugs). These white blood cell reductions were the result of marked decreases in absolute and relative neutrophil, monocyte and eosinophil counts. In addition, mild to moderate decreases in hemoglobin, hematocrit and platelet counts were noted in groups 3 and 6. Group 4 animals, having received only one cycle of drug treatment, showed mean hematology values similar to those of the control on day 33 (with the exception of RDW and HDW). Following the 22 day recovery period (day 56), the hematological values for Group 4 animals were comparable to those of control animals, including RDW and HDW, suggesting that the hematological effects of CPX-351 are reversible.

Following the recovery period, there were no drug-related histopathological changes noted in the surviving group 4 dogs (with the exception of 1 animal showing moderate splenic lymphoid necrosis) suggesting that the findings associated with the administration of CPX-351 are partially or completely reversible. There were no drug-related histopathological changes observed in tissues from the control (group 1), vehicle (group 2) low dose CPX-351 (group 3) and comparative free-drug-treated (group 6) animals.

Whole blood copper concentrations in animals terminated early (days 7-9; group 5) were slightly elevated. By day 33, the copper levels in the treated dogs that survived had normal levels again, suggesting that copper is cleared from the blood of dogs receiving CPX-351.

TABLE 2

Summary of Repeat Dose Toxicological Studies with CPX-351

| Study # | Species/ strain (route) | Regimen | Duration of study | Evaluations | Group | Cytarabine Dose (mg/kg) | Daunorubicin Dose (mg/kg) Free base | Deaths/Total M | F | comments |
|---|---|---|---|---|---|---|---|---|---|---|
| 1005-0361 | rat/SD (iv) | 60 minutes infusion days 1, 3, 5 and 22, 24, 26 | 29-57 days | mortality, clinical signs, body weight, food consumption, ophthalmoscopy, hematology, serum chemistry (copper), urinalysis, gross pathology, micro pathology groups 1, 4; toxicokinetics | 1 saline<br>2 CPX-351<br>3 CPX-351<br>4 CPX-351 | 0<br>5<br>10<br>15 | 0<br>2.2<br>4.4<br>6.6 | 1/15<br>1/10<br>8/10<br>15/15 | 0/15<br>3/10<br>7/10<br>15/15 | Unscheduled deaths in group 2 were not considered drug-related. Surviving animals in groups 2 and 3 showed marked reductions in WBC and RBC parameters. |
| 1005-0372 | dog/ beagle (iv) | 60 minutes infusion days 1, 3, 5 and 22, 24, 26 | 29-57 days | mortality, clinical observations, body weight, food consumption, ophthalmoscopy, EKG, hematology, serum chemistry (copper), urinalysis, gross pathology, full micropathology; toxicokinetics | 1 saline<br>2 vehicle<br>3 CPX-351<br>4 CPX-351<br>5 CPX-351<br>6 Free** | 0<br>0<br>1<br>2<br>3<br>2 | 0<br>0<br>0.44<br>0.88<br>1.32<br>0.88 | 0/5<br>0/3<br>0/3<br>1/3*<br>5/5*<br>0/3 | 0/5<br>0/3<br>0/3<br>1/3*<br>5/5*<br>0/3 | Dogs terminated early showed GI signs, internal hemorrhaging and severe bone marrow hypocellularity. Surviving dogs in group 4 received one cycle of treatment only and showed no drug-related adverse effects on day 34. Decreased WBC in groups 3 and 6 on day 33. |

*Animals found dead or terminated moribund Days 7-12.
**Animals receiving the "free" drugs received commercial cytarabine by IV infusion over one hour followed by a slow, IV push injection of commercial daunorubicin.

EXAMPLE 2

Clinical Phase I Trial

Physical, Chemical and Pharmaceutical Information. CPX-351 is a liposomal formulation of a fixed combination of the antineoplastic drugs cytarabine and daunorubicin. The two drugs are present inside the liposome in a 5:1 molar ratio shown to have non-antagonistic activity in preclinical studies. The liposome membrane is composed of distearoylphosphatidylcholine, distearoylphosphatidylglycerol and cholesterol in a 7:2:1 molar ratio. These liposomes have a nominal diameter of approximately 100 nm and are suspended in sucrose-phosphate-buffer at pH 7.4. Sterilization is achieved by filtration though a 0.22 µm filter.

CPX-351 is provided as a sterile, pyrogen-free, purple, opaque suspension of 5 mL in single-use, 10 mL glass vials and may also be provided as 20 or 25 mL suspensions in 50 mL glass vials. CPX-351 is stored frozen (−20° C.) and is thawed at room temperature for 60 minutes prior to dilution and administration. CPX-351 may also be lyophilized for storage and resuspended prior to administration. The dispersion is diluted in normal saline or dextrose for injection before intravenous administration to the patient.

Each 10 mL single-use vial of CPX-351 (Cytarabine:Daunorubicin) Liposome Injection provided 25 mg of cytarabine and 11 mg of daunorubicin. Each milliliter of the thawed formulation is listed in Table 3 below.

TABLE 3

Components of CPX-351 liposomal injection

| Component | mw | Amount per mL | Amount per unit |
|---|---|---|---|
| Cytarabine, USP | 243 | 5.0 mg | 1.0 mg |
| Daunorubicin USP(reported as the free base) | 528 | 2.2 mg | 0.44 mg |
| Distearoylphosphatidylcholine | 790 | 22.7 mg | 4.5 mg |
| Distearoylphosphatidylglycerol | 801 | 6.6 mg | 1.3 mg |
| Cholesterol, NF | 387 | 1.6 mg | 0.3 mg |
| Copper gluconate, USP | 454 | 4.6 mg | 0.9 mg |
| Triethanolamine, NF | 149 | 0.36 mg | 0.07 mg |
| Sucrose, NF | 342 | 125.5 mg | 25.1 mg |
| Sodium phosphate, monobasic, USP | 120 | 0.5 mg | 0.1 mg |
| Sodium phosphate dibasic, USP | 142 | 4.3 mg | 0.9 mg |
| Water for Injection USP, q.s. | | 1.0 mL | 0.2 mL |

Clinical Studies—Starting Dose. For cytotoxic antineoplastic agents, the usual starting dose for the first trial in humans is calculated on the basis of body surface area (mg/m$^2$) and is generally given as $1/10$ the $LD_{10}$ in rodents (if this dose is not severely toxic in non-rodents) or $1/3^{rd}$ the "Toxic Dose Low" (the lowest dose which produces drug-induced pathologic alterations in hematologic, chemical, clinical or morphologic parameters) in the most sensitive species if double this dose is not lethal and does not cause severe, irreversible toxicity. The $LD_{10}$ (based on the cytarabine dose) in rodents was approximately 10 mg/kg (60 mg/m$^2$), therefore $1/10^{th}$ equals 6 mg/m$^2$. The TDL in dogs was 1 mg/kg (20 mg/m$^2$) but double this dose (40 mg/m$^2$) was lethal. Therefore, $1/3^{rd}$ 20 mg/m$^2$ is equal to 6.7 mg/m$^2$, but use one half of this for safety ($1/6$ the highest non-lethal dose), thus, the starting dose based on this calculation is 3 mg/m$^2$. This is cytarabine 3 mg/m$^2$ and daunorubicin 1.32 mg/m$^2$ in the CPX-351 formulation.

Schedule. Standard remission induction regimens for AML generally consist of an anthracycline antibiotic for three days and cytarabine for 5 to 7 days. A day 1, 3 and 5 regimen, which is close to the standard regimens, is used.

CPX-351 was administered on days 1, 3 and 5 of each induction course. A second induction course was permitted if there was evidence of antileukemic effect and persistent leukemia in a 14 day bone marrow.

Infusion Times. Acute infusion-associated reactions (e.g. flushing, shortness of breath, headache, chills, back pain, tightness in the chest and/or hypotension) have been noted in large clinical trials of patients receiving liposomal chemotherapeutic agents. In most patients, these reactions resolve over several hours to one day once the infusion is terminated. In some patients, the reaction resolves by slowing the infusion rate. The following table (Table 4) compares the amount of lipid in several liposome products and in CPX-351. A 90-minute infusion time was chosen based on this information.

TABLE 4

Amount of lipid in liposome products

| Agent | Usual drug dose (mg/kg) | Lipid dose (mg/kg) | Infusion time (hours) | Lipid infusion rate (mg/kg/hour) |
|---|---|---|---|---|
| DaunoXome (40 mg/m$^2$) | 1.03 | 19.23 | 1 | 19.23 |
| Doxil (50 mg/m$^2$) | 1.28 | 10.26 | 1 | 10.26 |
| Myocet (60 mg/m$^2$) | 1.54 | 5.71 | 1 | 5.71 |
| CPX-351 (136 units/m$^2$) | 1.54 | 21.67 | 1.5 | 14.43 |

Assumptions:
Doxil recommended to start at an infusion rate of 1 mg/minute and then, if tolerated, the rate is increased to infuse over one hour.
Calculations are based on a 70 kg, 1.8 m$^2$ BSA patient.
CPX-351 dose assumed above would be a (136.4 mg Cytarabine: 60 mg Daunorubicin) per m$^2$ dose.

Dose Escalation and Levels. There is a 30+-year experience with the active moieties of CPX-351, cytarabine and daunorubicin, and the toxicities are well recognized. There is also significant experience with liposomal encapsulation of cytotoxic drugs (e.g., Doxil®, DaunoXome®, Myocet®) and in general, doses of the active moiety, when encapsulated, are not significantly different in toxicity from the free drug. Because of this experience and because exposure of patients with rapidly progressing disease to sub-optimal doses of therapeutic agents in phase 1 trials is not desirable, prior to start of the trial, we proposed an accelerated escalation schedule with a doubling of dose (early phase) and 50% dose increments (late phase) until toxicity or a pharmacodynamic effect was observed, and subsequent dose escalations proceeding at 33% increments (See Table 5A).

TABLE 5A

Proposed Dose Escalation of CPX-351

| Level | CPX-351 units/m$^2$ | Daunorubicin mg/m$^2$ | Cytarabine mg/m$^2$ | Phase |
|---|---|---|---|---|
| 1 | 3 | 1.32 | 3 | Early |
| 2 | 6 | 2.64 | 6 | Escalation by dose doubling |
| 3 | 12 | 5.28 | 12 | |
| 4 | 24 | 10.6 | 24 | |
| 5 | 48 | 21.1 | 48 | |
| 6 | 72 | 31.7 | 72 | Late |
| 7 | 108 | 47.5 | 108 | Escalation by 50% increments |
| 8 | 162 | 71.3 | 162 | |
| 9 | 243 | 107.0 | 243 | |

Dose Escalation in patients receiving CPX-351 Liposome Injection would occur in two phases. The early phase would begin at 3 units/m$^2$ (1 unit=1 mg cytarabine and 0.44 mg daunorubicin) with single patient cohorts and escalate with dose doublings until Dose Level 5 (48u/m$^2$), or until there was evidence of antileukemic activity or a pharmacodynamic (PD) effect defined as:

Bone marrow reduction in cellularity (>50% reduction, with reduction in blasts) and/or Non-hematologic treatment emergent event that is possibly, probably or definitely related to CPX-351 ($\geq$grade 2<DLT).

When a PD effect is seen; a second patient is entered in the cohort. If that patient also experiences a PD effect, then the dose escalations continue at 33% increments with three patients per cohort. If the second patient does not have a PD effect, then the escalation continues with one patient per cohort and dose doublings in the early phase and 50% increments in the late phase. The late phase escalation begins at Dose Level 6 (72u/m$^2$) with 50% dose escalations and single patients per cohort until a PD effect is seen as described above. If during the early or late phase escalation a DLT is observed in the first subject, up to 5 additional patients (not to exceed 6 patients) are entered and dose escalation will stop if a second patient experiences a DLT (see below). If no other patient experiences a DLT, dose escalation continues at 33% increments. If $\geq$2 patients treated at a given dose level experience DLT, then the MTD is considered to have been exceeded and three more patients are enrolled at the next lower dose level. Dose escalation to a subsequent dose level will not take place until the last patient in the previous level has been evaluated for at least 14 days after the last dose of each induction course; and if there is no evidence of potential hematologic DLT.

Dose escalations remain at 33% and have not increased to 50% increments as outlined in Table 5B below.

TABLE 5B

Actual Dose Escalation of CPX-351

| Level | CPX-351 units/m$^2$ | Daunorubicin mg/m$^2$ | Cytarabine mg/m$^2$ | Phase |
|---|---|---|---|---|
| 1 | 3 | 1.32 | 3 | Early |
| 2 | 6 | 2.64 | 6 | Escalation by dose doubling |
| 3 | 12 | 5.28 | 12 | |
| 4 | 24* | 10.6 | 24 | |
| 5 | 32 | 14.1 | 32 | Late |
| 6 | 43 | 18.9 | 43 | Escalation by 33% increments |
| 7 | 57 | 25.1 | 57 | |
| 8 | 76 | 33.4 | 76 | |
| 9 | 101 | 44.4 | 101 | |
| 10 | 134 | 59.0 | 134 | |

*PD effect was observed in two patients at the 24 unit/m2 dose level, subsequent cohorts entered 3 patients per cohort and dose escalations were reduced to 33%.

Repeat of Induction. Patients may receive a second course of induction at the same dose as the first induction if the bone marrow biopsy/aspirate at or around Study Day 14 indicates persistence of leukemia. No intra-patient dose escalation is permitted. If the bone marrow biopsy/aspirate indicates a <20% cellularity and <5% blasts, a repeat bone marrow biopsy/aspirate must be obtained 5-7 days later if persistent leukemia is uncertain and aplasia is still considered possible. Patients with aplasia (<20% cellularity and <5% blasts) are observed for hematopoietic recovery and for toxicity up to about Study Day 42 or until the initiation of consolidation therapy. Patients with residual leukemia may receive a second induction provided there is evidence of substantial antileukemic effect following the first induction. If a second induction is administered the patient is followed for up to around 42 days after the start of the second induction course.

Disease Assessment Criteria. For AML, ALL, refractory anemia with excess blasts or excess blasts in transformation, complete remission requires normalization of peripheral blood neutrophils to ≧1000/dL, platelets to more than 100,000/dL and normocellular bone marrow with less than 5% blasts with no Auer rods. If Auer rods are present with less than 5% blasts then the response is considered partial. Responses are considered partial if there is normalization in peripheral blood neutrophil and platelet counts but 6-25% blasts persist in bone marrow.

Response Duration. Response duration is measured from the time measurement criteria for CR or PR are first met until the first date that recurrent or progressive disease is objectively documented.

Results. This study is a non-randomized open-label, single-arm, dose escalating phase 1 trial. Study enrollment duration to date took approximately 18 months. 33 subjects (22 Male:11 Female), median age 62 y (24-81), all with prior therapy, enrolled in 10 cohorts. Demographics and disposition of the first 10 cohorts are summarized in Table 6 below:

As is typical with phase I clinical trials, the patients in this phase I population were heavily pretreated patients that had no alternative treatment options. Results for these leukemia patients at doses were we began achieving therapeutic responses are summarized below in Table 7. In Table 7 the following abbreviations are used: "CR" represents "complete remission"; "PR" represents "partial remission"; "CRp" represents "complete remission with incomplete platelet recovery" (ie. a failure to achieve platelet recovery greater than or equal to 100,000/µL by Study Day 42); "BMT" represents "bone marrow transplant"; "PD" represents pharmacodynamic (PD) effect defined as:

Bone marrow reduction in cellularity (>50% reduction, with reduction in blasts) and/or Non-hematologic treatment emergent event that is possibly, probably or definitely related to CPX-351 (≧grade 2<DLT).

As demonstrated by the results, therapeutic responses were observed with as little as 32 units/m² of CPX-351 being administered and surprisingly continued to be observed over almost all dose levels up to and including 134 units/m².

TABLE 6

Demographics and disposition of the phase I clinical trial for CPX-351

| | | Cohort No. | | | | | | | | |
| --- | --- | --- | --- | --- | --- | --- | --- | --- | --- | --- |
| | | 1-3 | 4 | 5 | 6 | 7 | 8 | 9 | 10 | Total |
| | | dose (U/m2) | | | | | | | | |
| zebra | | 3-12 n = 4 | 24 n = 4 | 32 n = 4 | 43 n = 4 | 57 n = 3 | 76 n = 3 | 101 n = 5 | 134 n = 6 | 33 |
| Gender | Male | 3 | 3 | 4 | 0 | 2 | 3 | 3 | 4 | 22 |
| | Female | 1 | 1 | | 4 | 1 | | 2 | 2 | 11 |
| Age (yr) | Median | 52.5 | 60.5 | 64 | 70 | 61 | 60 | 57 | 65 | 62 |
| | Min-Max | 25-78 | 50-76 | 55-73 | 44-77 | 24-66 | 46-72 | 49-77 | 34-81 | 24-81 |
| | ≧60-75 | 1 | 1 | 3 | 2 | 2 | 2 | 1 | 4 | 16 |
| | >75 | 1 | 1 | | 1 | | | 1 | 1 | 5 |
| Race | Caucasian | 3 | 3 | 3 | 4 | 1 | 2 | 4 | 6 | 26 |
| | Black | 1 | | | | | 1 | | | 2 |
| | Asian | | | 1 | | 2 | | 1 | | 4 |
| | Other | | 1 | | | | | | | 1 |
| ECOG | 0 | | 3 | | | 1 | 1 | 1 | 5 | 4 | 11 |
| | 1 | | | 4 | 2 | 2 | 2 | 2 | | 2 | 12 |
| | 2 | 1 | | | 2 | 1 | | | | 4 |
| Type of Leukemia at Diagnosis | AML | 1 | 4 | 4 | 2 | 3 | 3 | 5 | 6 | 28 |
| | Secondary AML | | | | | 1 | | | | 1 |
| | MDS → AML | 1 | | | | | | | | 1 |
| | ALL | 2 | | | 1 | | | | | 3 |
| Response to Last Therapy | None | 4 | 2 | 3 | 2 | 3 | 1 | 4 | 4 | 23 |
| | CR | | 2 | 1 | 2 | | 2 | 1 | 2 | 10 |
| | UNK | | | | | | | | | |
| On Study | Adverse Event | | 1 | | 1 | | | 2 | 1 | 5 |
| Reason Off Study | Persistent Leukemia | 4 | 4 | 4 | 2 | 2 | 4 | 2 | 3 | 25 |
| | Bone Marrow Transplant | | | | | | | 1 | | 1 |
| Current Status | Alive | | | | | | | | | |
| | Persistent Leukemia | | | 2 | | 1 | 1 | 2 | 3 | 9 |
| | Complete Remission | | | | 1 | | | | 1 | 2 |
| | Unknown | | | | | | | | 1 | 1 |
| | Deceased | | | | | | | | | |
| | 2' to leukemia | 3 | 4 | 2 | 3 | 2 | 1 | 3 | | 18 |
| | Study drug related | | | | | | | | 1 | 1 |
| | Unknown | | 1 | | | | 1 | | | 2 |

TABLE 7

Results of phase I clinical trial for CPX-351

| Patient | Dose | Prior Therapies Drug | Outcome | CPX-351 Inductions | Best Response |
|---|---|---|---|---|---|
| 02-003<br>63yo M<br>AML-M5 | 32 | Cytarabine/daunorubicin<br>Cytarabine/daunorubicin<br>HiDAC<br>5-azacytidine<br>Claridibine | No Response<br>CR 4-mons.<br><br><br>No Response | 2 | PR |
| 03-006<br>55yo M<br>AML | 32 | Cytarabine/daunorubicin<br>Cytarabine/daunorubicin<br>HiDAC | CR 2 mons.<br>CR 9 mons.<br>CR 10 mons. | 2 | CRp |
| 02-004<br>AML-M4 | 32 | Decitabine<br>SNS-595<br>Triciribine | No Response<br>No Response<br>No Response | 1 | No Response |
| 03-007<br>77yo F<br>AML | 43 | Zarnestra/etoposide<br>Cytarabine/daunorubicin<br>KW2449 | CR- UNK mons.<br>No Response<br>No Response | 1 | No Response |
| 03-008<br>74yo F<br>AML | 43 | Zarnestra<br>Arsenic/Ara-C<br>Lintuzumab | No Response<br>CR 7-mons.<br>No Response | 1 | CR |
| 01-002<br>44yo F<br>ALL | 43 | Cyclophosphamide/Daunorubicin/<br>Dexamethasone/vincristine/L-aspar.<br>Gleevec/methotrexate<br>HSCT | CR-8 mons. | 1 | CR |
| 02-005<br>66yo F<br>2° AML | 43 | Cytarabine/daunorubicin/etoposide<br>Claridibine/cytarabine | CR- 4 mons. | 1 | No Response |
| 01-003<br>61yo M<br>AML | 57 | Cytarabine/daunorubicin<br>Cytarabine/daunorubicin (re-induc)<br>HiDAC<br>Idarubicin/Cytarabine/EL625 | No Response<br>CR- 7 mons.<br><br>No Response | 1 | No Response |
| 03-009<br>24yo F<br>AML | 57 | Cytarabine/daunorubicin<br>HiDAC<br>MEC<br>Clofarabine/Cytarabine | No Response<br>No Response<br>No Response<br>No Response | 2 | No Response |
| 03-010<br>66yo M<br>AML | 57 | Arsenic/Ara-C<br>Cytarabine/daunorubicin 7 + 3, 5 + 2<br>Zarnestra | No Response<br>CR- 4 mons.<br>No Response | 2 | No Response |
| 03-011<br>60yo M<br>AML | 76 | Cytarabine/daunorubicin<br>Cytarabine/daunorubicin<br>Cytarabine/daunorubicin | CR- 4 mons. | 1 | CR |
| 02-006<br>46yo M<br>AML | 76 | Cytarabine/daunorubicin<br>HiDAC<br>Cytarabine/etoposide | CR- 3 mons. | 1 | No Response |
| 03-012<br>72yo M<br>AML | 76 | Cytarabine/daunorubicin | No Response | 1 | No Response |
| 02-007<br>68yo M<br>AML | 101 | Daunorubicin/Cytarabine<br>HiDAC<br>FLAG + Idarubicin<br>Mylotarg<br>Mitoxantrone/Cytarabine<br>Triciribine | CR- 7 mons.<br><br>No Response<br>No Response<br>No Response<br>No Response | 1 | Aplasia-died |
| 03-013<br>77yo F<br>AML | 101 | Zarnestra/etoposide | CR-14 mons. | 1 | Aplasia-died |
| 02-008<br>49yo M<br>AML | 101 | Daunorubicin/Cytarabine<br>Clofarabine/Cytarabine | No Response<br>No Response | 1 | Scheduled for BMT |
| 03-014<br>55yo F<br>AML | 101 | Cytarabine/idarubicin<br>MEC<br>Mylotarg<br>FLAG + idarubicin<br>Vidaza/HiDAC | No Response<br>No Response<br>No Response<br>No Response<br>No Response | 2 | No Response |
| 02-009<br>57yo M<br>AML | 101 | Daunorubicin/Cytarabine<br>HiDAC | No Response<br>No Response | 2 | PR |
| 03-015<br>67yo F<br>AML | 134 | Idarubicin/Cytarabine<br>HDAC | CR-4 yr. 8 mons | 1 | CR |
| 02-010<br>34yo M<br>AML | 134 | Daunorubicin/Cytarabine<br>Claridibine/Cytarabine | No Response<br>No Response | 1 | PD |
| 01-004<br>81yo F<br>AML | 134 | Arsenic/Ara-C<br>Arsenic/Ara-C<br>Ara-C | No Response<br>CR-8 mons. | 1 | Aplasia-died |

TABLE 7-continued

Results of phase I clinical trial for CPX-351

| Patient | Dose | Prior Therapies Drug | Outcome | CPX-351 Inductions | Best Response |
|---|---|---|---|---|---|
| 01-005 59yo M AML | 134 | Daunorubicin/Cytarabine/Etoposide/ HSCT Idarubicin/Fludarabine Mylotarg/Dacogen | CR-11 mons. No Response No Response | 1 | PD |
| 03-016 68yo M AML | 134 | Arsenic/Ara-C Daunorubicin/Ara-C 7 + 3, 5 + 2 Ara-C | No Response No Response No Response | 2 | PD |
| 02-011 32yo M AML | 134 | Revlimid Daunorubicin/Ara-C 7 + 3, 5 + 2 | No Response No Response | 1 | Unknown |

EXAMPLE 3

CPX-351 Phase I Clinical Trial—Case Studies

Below are 5 case studies of patients treated in the ongoing CPX-351 Phase I Clinical Trial.

Case Study 1—AML patient responds to CPX-351 even though he did not respond to prior conventional 7/3 cytarabine/daunorubicin treatment): Patient 02-011 a 62 year old male diagnosed with AML in 2007 received initial Revlimid therapy from September-November 2007 and showed no response. In December 2007, he was administered the standard conventional 7+3 cytarabine/daunorubicin treatment but again did not respond. Analysis of his bone marrow 14 days after the conventional 7+3 cytarabine/daunorubicin treatment began showed 5% cellularity and 24% blasts. The patient was immediately enrolled in the CPX-351 Phase I Clinical Trial and received 134 units/m$^2$ of CPX-351 on a day 1, 3 and 5 schedule beginning Jan. 2, 2008. Analysis of his bone marrow 15 days later showed aplasia (<10% Cellularity, <5% Blasts).

Case Study 2—Heavily pretreated AML patient achieves complete response following CPX-351 treatment: Patient 03-015 a 67 year old female received Idarubicin/Cytarabine treatment in May 2002 as well as high-dose ara-C (or cytarabine) also called, HDAC, consolidation treatment from June-August 2002. The patient achieved a complete response (CR) which lasted for 4 years and 8 months. The patient relapsed and on Oct. 29, 2007 she was enrolled in the CPX-351 Phase I Clinical Trial and received 134 units/m$^2$ of CPX-351 on a day 1, 3 and 5 schedule. Analysis of her bone marrow 15 days later showed <10% cellularity. The patient achieved a CR 42 days after she began taking CPX-351. The only adverse effects recorded were bleeding gums and grade 3 rash around days 10-15 after starting on CPX-351.

Case Study 3—AML patient unable to receive conventional 7+3 cytarabine/daunorubicin therapy due to age, poor health and an expected lack of tolerance to highly cytotoxic treatments achieves complete response with minimal adverse affects following CPX-351 induction therapy: Patient 03-008 a 74 year old female received light prior therapy because of her age and expected inability to tolerate highly cytotoxic conventional therapies. She was treated from April 2004-April 2006 with Zarnestra and had no response. From May 2006-February 2007 she received induction therapy with Arsenic/cytarabine and achieved a CR which lasted for 7 months. The patient relapsed and from March 2007-April 2007 was put on Lintuzumab but had no response. The patient was enrolled in the CPX-351 Phase I Clinical Trial and beginning on Apr. 30, 2007 received three doses of CPX-351 at 43 units/m$^2$. 35 Days after initiating CPX-351 treatment, the patient achieved a CR (3% blasts); the patient also received CPX-351 as consolidation therapy (given on days 1 & 3, with day 5 omitted) starting on day 52 after initial induction treatment. AML was not detectable at 204 days after initial CPX-351 treatment.

Case Study 4—AML patient scheduled for bone marrow transplant after CPX-351 treatment when unresponsive to conventional 7+3 cytarabine/daunorubicin treatment or Clofarabine/Cytarabine treatment: Patient 02-008 a 49 year old male received conventional 7+3 cytarabine/daunorubicin treatment and did not respond. The patient was then administered clofarabine/cytarabine treatment and also did not respond. The patient was then enrolled in the CPX-351 Phase I Clinical Trial and on Sep. 24, 2007 he began taking CPX-351 at 101 units/m$^2$. 15 Days after his initial CPX-351 treatment, bone marrow analysis showed 5% cellularity and 16% blasts and at Day 29 he was scheduled for a bone marrow transplant. The only adverse effects reported were fatigue and grade 1 rash at day 8 after initial CPX-351 treatment. This patient in particular demonstrates the potential use of CPX-351 as a bone marrow conditioning agent.

Case Study 5—ALL patient heavily pretreated with prior therapies achieves complete response with CPX-351 treatment: Patient 01-002 a 44 year old female received cyclophosphamide/daunorubicin followed by Dexamethasone/vincristine/L-asparagine as part of a hematopoietic stem cell transplant conditioning therapy from March-April 2006 and achieved a CR which lasted for 8 months. The patient was later enrolled in the CPX-351 Phase I Clinical Trial and on May 7, 2007 started CPX-351 at 43 units/m$^2$. 12 Days following initial infusion bone marrow analysis showed cellularity <10% and blasts 0% and a CR was recorded at Day 43 following initial CPX-351 treatment. This patient in particular demonstrates the potential use of CPX-351 in acute lymphoblastic leukemia.

EXAMPLE 4

CPX-351 Phase I Clinical Trial—Pharmacokinetics

Objectives of the Pharmacokinetics (PK) Analysis of the Study
  To determine single dose and multiple dose pharmacokinetics of cytarabine and daunorubicin, and selected metabolites (Ara-U and daunorubicinol) following administration of CPX-351 in leukemic patients.
  To gather preliminary information on overall exposure, dose proportionality, and accumulation of CPX-351 in cancer patients.

To establish, if possible, a correlation between intensity of exposure to CPX-351 components and effect (safety and efficacy).

PK Sampling Scheme. Plasma samples for PK analysis were collected on days 1, 3 and 5 of the first cycle. Blood samples (approximately 7 mL) were collected from a peripheral vein in the arm contralateral to the arm used for infusion and placed in tubes containing ethylene diamine tetraacetic acid (EDTA) as anticoagulant. Samples were collected at the following times (relative to the start of the infusion) during the first induction:

Prior to dosing on Day 1, during the infusion at 45 minutes (or the mid-point of the infusion) and 90 minutes (or at the end of the infusion), then at 2, 4, 6, 8, 12 and 24 hours relative to the start of infusion.

Prior to dosing on Day 3, during the infusion at 45 and 90 minutes.

Prior to dosing on Day 5, during the infusion at 45 minutes (or the mid-point of the infusion) and 90 minutes (or at the end of the infusion), then at 2, 4, 6, 8, 12, 24, 48, 72, 96, and 168 hours relative to the start of infusion.

Pharmacokinetic Analysis. Plasma samples were analyzed for cytarabine, daunorubicin, and the metabolites ara-U and daunorubicinol by LC-MS/MS using validated and specific high performance liquid chromatographic mass spectrometric methods. Plasma concentration-time profiles were generated for cytarabine and daunorubicin for each patient. Pharmacokinetic parameters were estimated from the plasma concentration-time profile of all evaluable patients. Using non-compartmental methods and WinNonlin® Professional (Version 4.0 or higher), pharmacokinetic parameters that can be calculated include, but are not limited to, the following:

| | |
|---|---|
| Cmax | Maximum observed concentration |
| Tmax | Time of occurrence of Cmax |
| $\lambda z$ | Elimination rate constant obtained from a linear regression of the natural log (ln) transformed concentration versus time data in the terminal phase (following dosing on Day 5 only) |
| $t^{1/2}$ | Terminal half-life, calculated as $\ln(2)/\lambda z$ |
| AUC (0-last) | Area under the plasma concentration-time curve from time zero to the time of the last post-dose quantifiable plasma concentration, obtained by the linear trapezoidal method |
| AUC (0-inf) | Area under the plasma concentration-time curve from time zero extrapolated to time infinity |
| CL | Systemic clearance computed as Dose/AUC(0-inf) (for cytarabine and daunorubicin only on Study Day 5) |

Compartmental methods of pharmacokinetic analysis may also be employed to evaluate metabolite disposition kinetics and/or to perform pharmacokinetic/pharmacodynamic modeling.

Figure 1A:
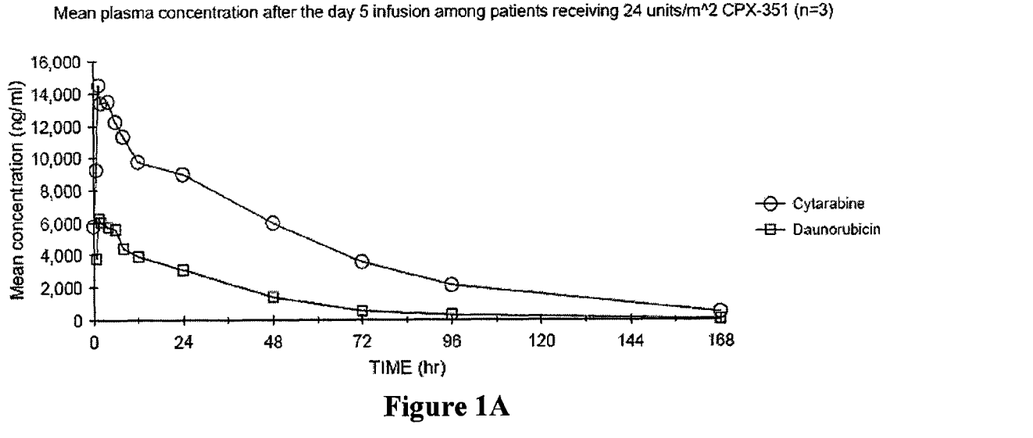
Figure 1B:
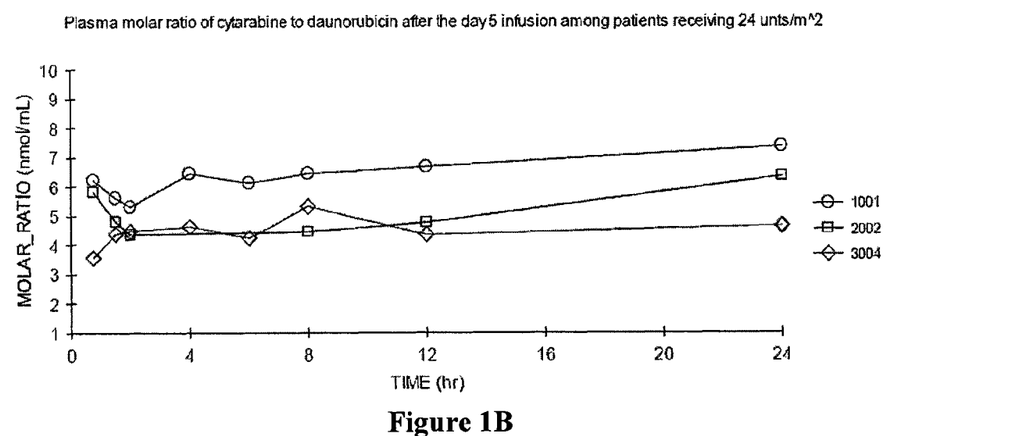
Figure 1C:
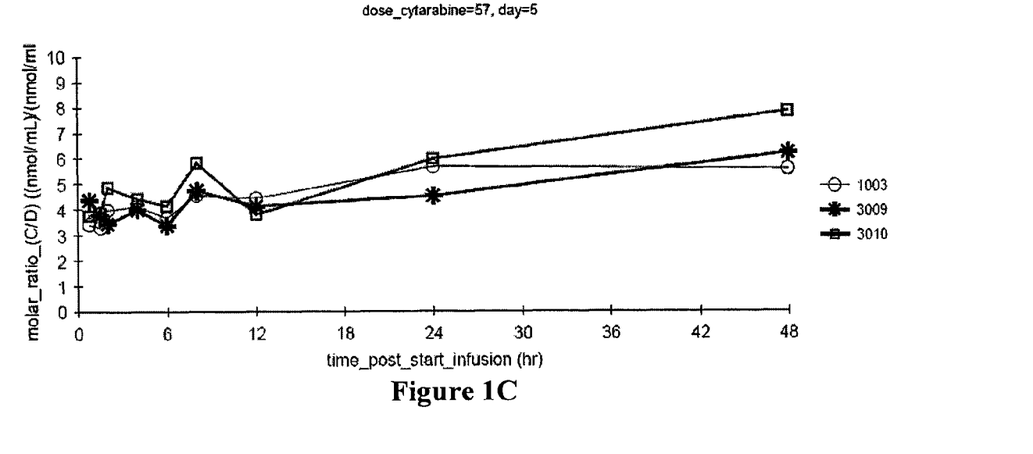

Descriptive statistics (mean, SD, CV %, median, min, and max) can be used to summarize the plasma concentration and the PK parameters as well as other analyses as appropriate for each treatment cohort. Pharmacokinetic analysis to date is summarized in FIG. 1. FIG. 1A shows the mean plasma concentration of cytarabine and daunorubicin up to 7 days after the day-5 infusion among patients receiving 24 units/m² of CPX-351 (N=3). FIG. 1B shows the plasma molar ratio of cytarabine to daunorubicin up to 24 hours after the day-5 infusion among patients receiving 24 units/m² of CPX-351 (N=3). As seen in the figure, in all subjects analyzed, the 5:1 molar ratio of cytarabine to daunorubicin was maintained near 5:1 for at least 24 hours. FIG. 1C shows the plasma molar ratio of cytarabine to daunorubicin up to 48 hours after the day-5 infusion among patients receiving 57 units/m² of CPX-351 (N=3). The graph in FIG. 1C clearly demonstrates that the molar ratio of cytarabine to daunorubicin was maintained at about 5:1 in the patients' blood for at least about 48 hours.

The invention claimed is:

1. A method to treat a leukemia in a human patient, said method comprising administering intravenously to said patient a pharmaceutical composition comprising cytarabine and daunorubicin at a fixed, molar ratio of cytarabine to daunorubicin of about 5:1 in an administration step of 8 hours or less,
   wherein said fixed ratio is maintained in the plasma for at least 4 hours, and
   wherein said fixed, molar ratio of cytarabine and daunorubicin is encapsulated in liposomes;
   wherein the composition is administered to provide cytarabine in an amount of 32-134 mg/m² and a total amount of 96-402 mg/m² in a cycle of administration consisting of a first administration step on day 1, a second administration step on day 3, and a third administration step on day 5; and
   wherein the liposomes comprise DSPC:DSPG:cholesterol at 7:2:1 molar ratio.

2. The method of claim 1 wherein the composition is administered in 3 hours or less for each administration step.

3. The method of claim 2, wherein the composition is administered in 90 minutes or less for each administration step.

4. The method of claim 1, wherein said administration is by intravenous (IV) drip.

5. The method of claim 1, wherein the leukemia is acute lymphocytic leukemia (ALL), acute myeloid leukemia (AML) or acute promyelocytic leukemia (APL).

6. The method of claim 1, wherein said subject has previously undergone at least one anti-cancer regimen, and/or has previously experienced a remission.

7. The method of claim 6 wherein said subject has experienced a relapse within 18 months after said anticancer regimen.

8. The method of claim 7 wherein said subject has experienced a relapse within 6 months after said anticancer regimen.

9. The method of claim 1, which further includes measuring a therapeutic effect as a function of increase in complete remission rate, and/or as a function of prolongation of complete remission duration and/or prolongation of time to progression and/or prolongation of survival.

10. The method of claim 1, which further includes measuring an improved safety result as a reduction in non-hematopoietic toxicities.

11. The method of claim 10, wherein the non-hematopoietic toxicities are mucositis and/or alopecia.

* * * * *